United States Patent [19]

Horizoe et al.

[11] Patent Number: 5,250,271

[45] Date of Patent: Oct. 5, 1993

[54] APPARATUS TO CONCENTRATE AND PURIFY ALCOHOL

[75] Inventors: Hirotoshi Horizoe, Hiroshima; Masura Maki, Kanagawa; Tetsuya Tanimoto; Masaki Yanagi, both of Hiroshima, all of Japan

[73] Assignee: Minister of International Trade & Industry, Tokyo, Japan

[21] Appl. No.: 705,017

[22] Filed: May 16, 1991

Related U.S. Application Data

[62] Division of Ser. No. 332,933, Feb. 20, 1990, Pat. No. 5,053,563.

[30] Foreign Application Priority Data

Jul. 24, 1987 [JP] Japan .................. 62-183461
Jul. 24, 1987 [JP] Japan .................. 62-183462

[51] Int. Cl.$^5$ ............................................ B01D 11/04
[52] U.S. Cl. ............................. 422/260; 422/256; 568/916; 203/18; 203/DIG. 13
[58] Field of Search ........... 422/260, 256; 568/916; 202/168, 169; 203/DIG. 13, 68, 18

[56] References Cited

U.S. PATENT DOCUMENTS

| | | | |
|---|---|---|---|
| 2,201,550 | 5/1940 | Van Dijck et al. | 422/256 |
| 2,597,009 | 5/1952 | Lobo et al. | 568/916 |
| 2,717,854 | 9/1955 | Felix | 422/260 |
| 2,879,272 | 3/1959 | Pennington | 422/260 |
| 2,911,361 | 11/1959 | Kleiss | 422/260 |
| 3,658,656 | 4/1972 | Adica et al. | 203/68 |
| 4,333,740 | 6/1982 | Priegnitz | 568/916 |
| 4,469,903 | 9/1984 | Schmidt | 568/916 |
| 4,492,808 | 1/1985 | Hagen et al. | 568/916 |
| 4,508,928 | 4/1985 | Victor | 568/916 |
| 4,636,284 | 1/1987 | English et al. | 203/18 |
| 4,744,869 | 5/1988 | Saito et al. | 203/DIG. 13 |
| 4,842,693 | 6/1989 | Wheldon | 202/169 |
| 4,956,052 | 9/1990 | Hirata et al. | 568/916 |

FOREIGN PATENT DOCUMENTS

| | | |
|---|---|---|
| 0234932 | 9/1987 | European Pat. Off. . |
| 56-56201 | 5/1981 | Japan . |
| 176919 | 10/1982 | Japan . |
| 62-25983 | 2/1987 | Japan . |
| 62-25982 | 3/1987 | Japan . |
| 62-25985 | 3/1987 | Japan . |
| 62-135440 | 6/1987 | Japan . |
| 62-29990 | 7/1987 | Japan . |

OTHER PUBLICATIONS

*Industrial and Engineering Chemistry Research*, vol. 26, No. 2, pp. 254–261, Feb., 1987, Brignole, et al.

Primary Examiner—James C. Housel
Assistant Examiner—Hien Tran
Attorney, Agent, or Firm—Baker & Daniels

[57] ABSTRACT

A method and an apparatus to condense and rectify alcohol, and more particularly to a method and an apparatus suitable for the energy-saving condensation and rectification of high-purity alcohol from the synthesized alcohol, the used alcohol aqueous solution in food industry and the fermented alcohol.

The method makes it possible to extract and recover alcohol of 99 wt % or higher with small quantity of propane solvent, using the propane in supercritical or pseudocritical conditions in the process of condensation and recovery of alcohol from aqueous solution of alcohol. Further, the method makes it possible to condense alcohol to the concentration of 95 wt % or higher by increasing the selectivity of alcohol through the cooling of the propane to liquid state.

1 Claim, 2 Drawing Sheets

APPARATUS TO CONCENTRATE AND PURIFY ALCOHOL

This is a division of application Ser. No. 07/332,933, filed Feb. 20, 1990, now U.S. Pat. No. 5,053,563.

TECHNICAL FIELD OF THE INVENTION

The present invention relates to a method and an apparatus to concentrate and purify alcohol, and more particularly to the method and apparatus suitable for the concentration and purification of high-purity alcohol from the synthesized alcohol, the used alcohol aqueous solution in food industry and the fermented alcohol in the energy-saving manner.

TECHNICAL BACKGROUND

The fermented alcohol produced from carbohydrates such as sweet potato, potato, corn, etc. is an important material for making various drinks and for industrial applications. Because alcohol concentration produced by fermentation is as low as 10~20 wt %, it is necessary to condense it to about 95~100 wt %.

Conventionally, the distillation method has been used for this concentration. However, this method is economically disadvantageous because much energy is consumed in heating the water - main component of this material — to 80°~100° C., and there is a strong demand on the development of an energy-saving method of concentration to replace the conventional means.

On the other hand, it has been proposed to use the energy-saving method to extract, separate and concentrate alcohol from water, using carbon dioxide in supercritical or pseudocritical condition. (Japanese provisional patent publications No. 56-56201 and 59-141528).

However, there is some restrictions to the selective extraction of alcohol when carbon dioxide is used as solvent. Maximum concentration is limited to about 91 wt %, and it is impossible according to the recent report to condense beyond this limit. Also, a large quantity of carbon dioxide (more than 15 weight parts of $CO_2$ to 1 weight part of 10% aqueous solution of alcohol) is needed because the solubility of alcohol in carbon dioxide is not high enough, and it is earnestly wanted to solve this problem.

As the result, there is a strong demand on the development of a new method and an apparatus to increase alcohol concentration and to raise alcohol solubility.

The purpose of the present invention is to provide the economical method and apparatus to concentrate and purify alcohol, by which it is possible to increase alcohol concentration to more than 91 wt % and to concentrate and recover alcohol by the use of small quantity of solvent.

DISCLOSURE OF THE INVENTION

The first object of this invention is to provide the method to concentrate and purify alcohol, wherein aqueous solution of alcohol is supplied from the raw material inlet in the middle of countercurrent flow extractor, the propane solvent is supplied from lower portion of said countercurrent flow extractor, said propane solvent is maintained in supercritical or pseudocritical conditions at the portion lower than said raw material inlet, while the propane solvent is maintained in liquid state at the portion higher than said raw material inlet, and the concentrated alcohol, virtually separated from water, is recovered from the upper portion of said countercurrent flow extractor.

The second object of the invention is to offer a method to concentrate and purify alcohol, wherein aqueous solution of alcohol is supplied from the raw material inlet in the middle of countercurrent flow extractor, the propane solvent is supplied form the lower portion of said countercurrent flow extractor, said propane solvent is maintained in supercritical or pseudocritical conditions at the portion lower than said raw material inlet, the propane solvent is maintained in liquid state at the portion higher than said raw material inlet, the propane solvent phase containing the concentrated alcohol, virtually separated from water, is withdrawn from the upper portion of said countercurrent flow extractor, the propane solvent is sent into propane solvent distillation tower, the propane liquid containing alcohol but no water is recovered from the bottom of said distillation tower, the propane gas containing water but no alcohol is recovered from the top of said distillation tower, the compression heat produced by the pressurization of said propane gas is used as heat source for said propane solvent distillation tower, a part thereof is returned to said propane solvent distillation tower and the remainder is sent again to the lower portion of said countercurrent flow extractor either directly or after indirect heat exchange with the upper fluid in said countercurrent flow extractor.

The third object of the invention is to offer an apparatus to concentrate and purify alcohol, comprising a inlet for aqueous solution of alcohol provided at the middle, a heavy liquid outlet at the bottom, and a light liquid outlet at the top, and further comprising a countercurrent flow extractor incorporating a propane solvent inlet line playing the role of a heat exchanger to lead the propane solvent in supercritical or pseudocritical conditions to the lower distributor from the upper portion, a propane solvent pressure distillation tower connected with said light liquid outlet line through a pressure reducing valve and furnished with propane solvent outlet at the top and with a concentrated alcohol outlet at the bottom, and a line to make said propane solvent drawing line connect with the propane solvent supply line of said countercurrent flow extractor through the booster and the bottom of said propane solvent distillation tower.

The present invention can be applied for the concentration and purification of all types of aqueous solution of alcohol. If an example is taken on fermented alcohol, alcohol concentration is about 10 wt %, and the remainder is water and the impurities in trace quantity such as fusel oil, etc.

The supercritical condition of propane as described in the present invention is the condition, where temperature and pressure are maintained more than $Tc = 96.8°$ C. and $Pc = 42$ atm. respectively. The pseudocritical condition of propane is defined as the condition, where the temperature is lower than the critical temperature $(Tc)$ but is higher than about 90° C., and the pressure is maintained at higher than the saturated vapor pressure of propane at such temperature.

The liquid state of propane as mentioned in the present invention is the condition, where the temperature is kept at about 70° C. or lower, and the pressure is maintained at higher than the saturated vapor pressure at such temperature.

BRIEF DESCRIPTION OF DRAWINGS

In the following, an embodiment of the present invention will be described in detail according to FIG. 1 to FIG. 3, where the same parts are indicated by the same numbers.

In FIG. 1 to FIG. 3, (1) shows the countercurrent flow extractor (which may be desirably a packed column, a plate column or a multistage extraction column), and (2) indicates the feed line of the raw material i.e. aqueous solution containing alcohol. (3) shows the feed line of propane solvent, and (4) denotes the drawing line for heavy liquid (having water as main component) at lower portion of the countercurrent flow extractor (1). (5) indicates the drawing line of light fluid (propane solvent and condensed alcohol) at the upper portion of the countercurrent flow extractor (1) and (6) is the alcohol concentration stage located above the raw material supply line (2). (7) is the alcohol recovery stage located below the raw material supply line (2), and (8) indicates a portion the propane solvent feed line.

In FIG. 2, (8) is the propane solvent feed line and plays the role of a heat exchanger at the same time. (9) is a distributor at the propane solvent outlet, and (10) is a pressure reduction valve. (11) is a propane solvent distillation tower, and (12) is a drawing line of propane solvent. (13) is a drawing line of concentrated alcohol and (14) is a booster pump. (15) is a heater for the propane solvent distillation tower, and (16) is a bypass line. (17) is a recirculation line for propane solvent, and (18) is a propane solvent line connected with the propane solvent feed line (3).

Figure 1:
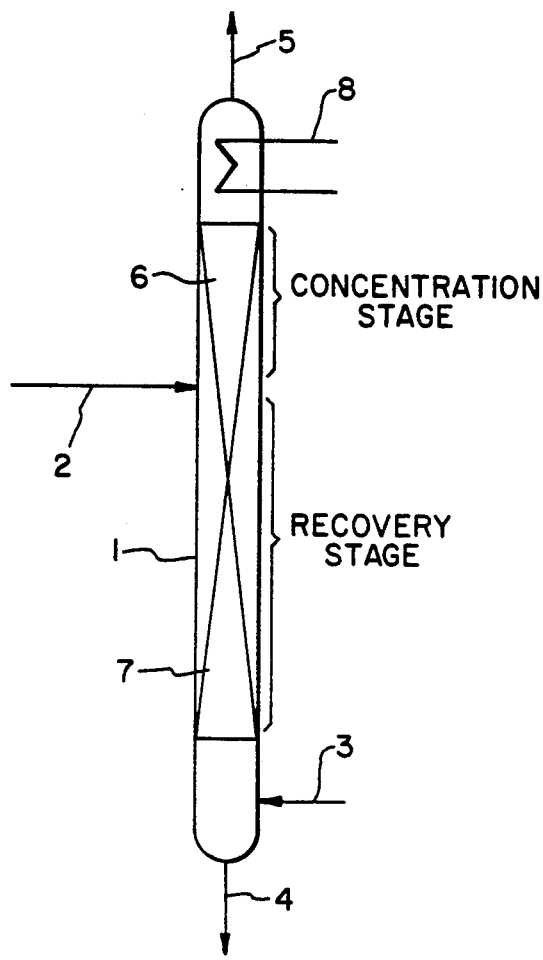
FIG. 1 and FIG. 2 show the process flow needed for the execution of this invention, and FIG. 3. is a partial enlargement of the countercurrent flow extractor shown in FIG. 2.

One weight part of aqueous solution of alcohol is supplied from the raw material feed line (2) and 3 to 10 weight parts of the propane solvent is supplied from the supply line (3) to the countercurrent flow extractor (1). Said propane solvent is brought into countercurrently contacting with aqueous solution of alcohol at the recovery stage (7) under supercritical or pseudocritical conditions, and the propane solvent phase with low density selectively extracts alcohol from aqueous solution of alcohol when it goes up, and it is taken out as light liquid from the light liquid drawing line (5).

The present inventors have found that the solubility of alcohol to propane is extensively increased and that the quantity of propane solvent needed to prevent the loss of alcohol from the heavy liquid drawing line (4) can be greatly reduced by maintaining the propane solvent under supercritical or pseudocritical conditions at the recovery stage (7).

The temperature should be desirably kept to about $90° \sim 170°$ C. at the recovery unit (7), and most desirably to $100° \sim 130°$ C. The pressure is maintained desirably at 50 atm. or more, and most desirably at $60 \sim 200$ atm. The pressure above this level is not desirable because the equipment cost may be increased.

Next, the inventors have found that water is selectively separated from the propane solvent phase when the latter is cooled down by the heat exchanger (8) for cooling at the alcohol concentration stage (6), and that the water goes down in the concentration stage (6) as heavy liquid, and alcohol in the propane solvent phase is concentrated to as high as $95 \sim 97$ wt % (containing no propane).

At the concentration stage (6), it is necessary to maintain such temperature and pressure that the propane solvent exists in liquid state. The temperature is desirably at $10° \sim 70°$ C., and most desirably between $10° \sim 60°$ C. It is desirable to maintain the pressure at the same level as that of the recovery unit (7).

On the other hand, the light liquid in the light liquid drawing line (5) consists of propane solvent and the concentrated alcohol. After pressure is reduced by the pressure reduction valve (10), the liquid is sent to the propane solvent distillation tower (11) to separate the propane solvent from concentrated alcohol. The concentrated alcohol is withdrawn from the line (13), while the propane solvent (12), containing virtually no alcohol, is pressurized again at the booster pump (14).

The pressure at the propane solvent distillation tower (11) should be desirably maintained at $10 \sim 40$ atm., and the temperature within the range of $10° \sim 80°$ C. As widely known in the field of chemical industry, it is desirable to separate alcohol from $H_2O$ and propane by designing said distillation tower in the form of multistage and/or packed column with recirculating a part of the propane solvent phase from the line (17) to the upper portion of said distillation tower (11).

The propane pressurized at the booster (14) can be effectively utilized as heat source for the propane solvent distillation tower (11) through the heat exchanger (15) because temperature level is raised due to adiabatic compression.

A part of propane is passed through the bypass line (16) for temperature adjustment and is connected to the line (18).

The temperature at the line (18) is at $10° \sim 95°$ C. A heat exchanger (8) is connected to the propane solvent feed line (3) of said countercurrent flow extractor (1) to perform indirect heat exchange countercurrently with the light liquid phase within said countercurrent flow extractor (1). Its outlet (9) is furnished at the bottom portion of said countercurrent flow extractor (1) so that the concentration stage (6) is cooled down for more effective concentration of alcohol.

Figure 3:
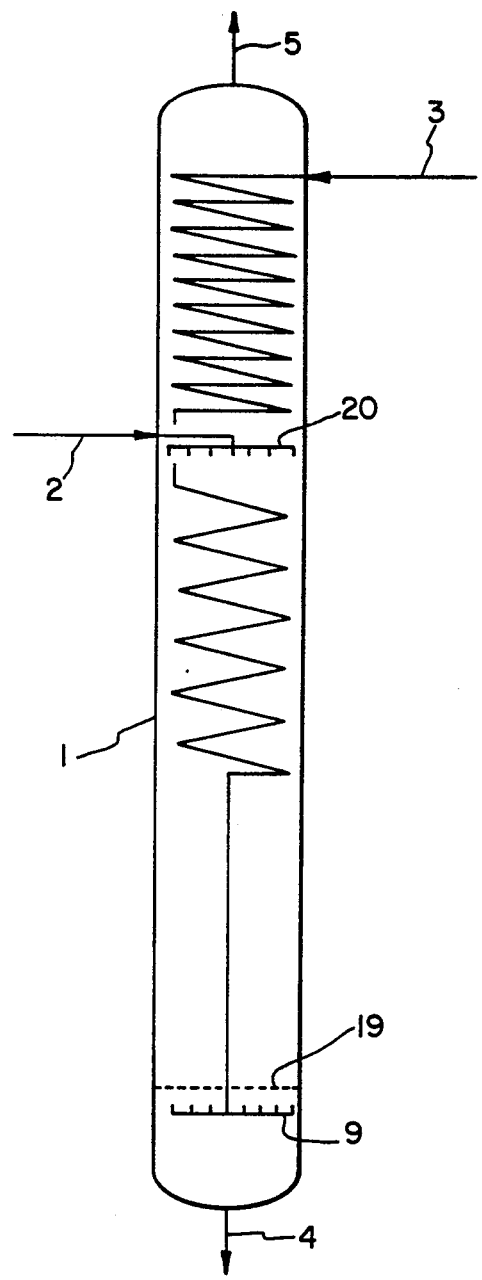
Figure 2:
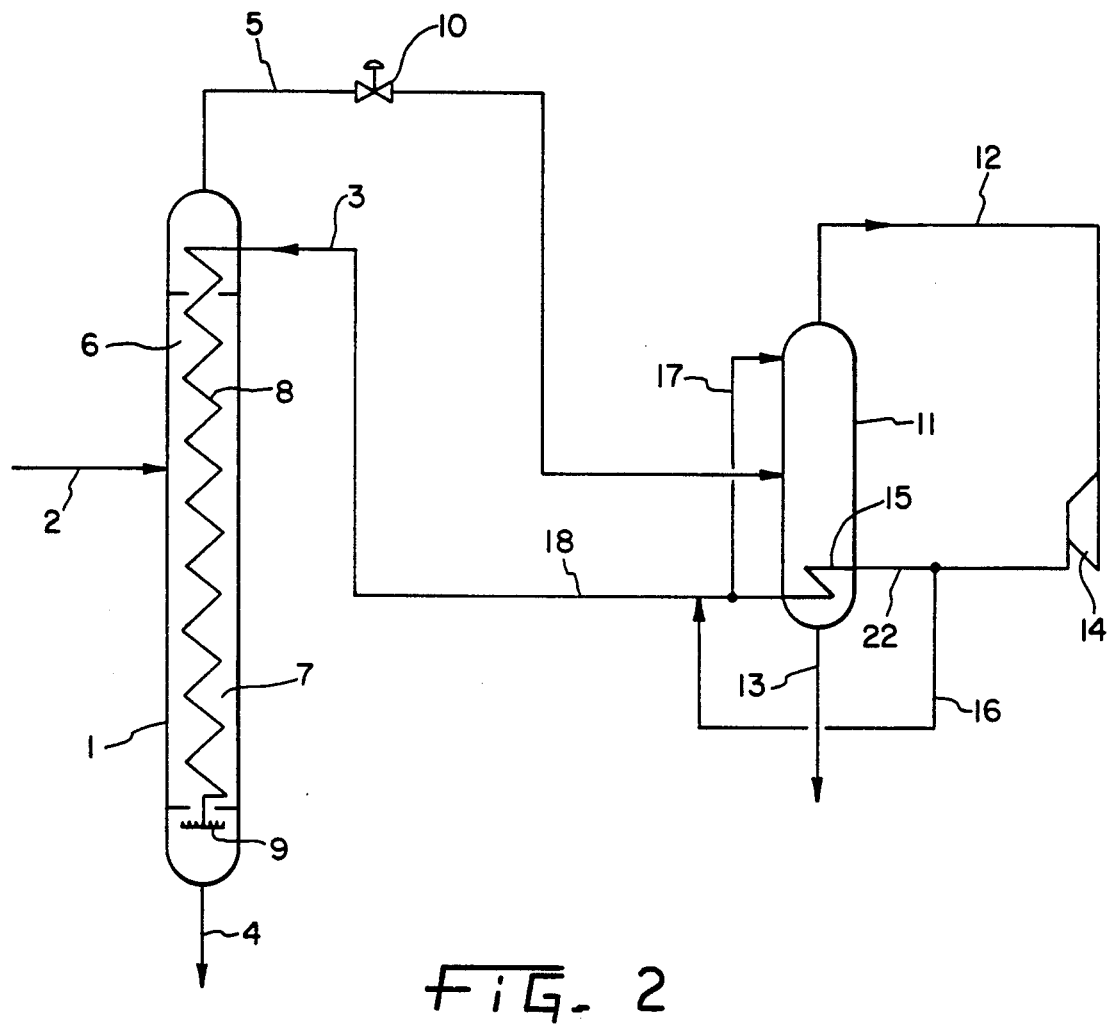

Said heat exchanger (8) should be desirably formed in the shape of spiral pipe as shown in FIG. 2, which indicates the countercurrent flow extractor (1) in detail, and the favorable temperature condition can be maintained by making it dense at the concentration stage (6) and sparse at the recovery stage (7). Specifically, the temperature can be maintained at $10° \sim 70°$ C. at the concentration stage (6) and at $90° \sim 170°$ C. at the recovery stage (7). In FIG. 3, (19) indicates the supporting plate for the filling materials in the countercurrent flow extractor (1), and (20) is a distributor for the raw material, i.e. aqueous solution of alcohol.

The Best Form Suitable for the Execution of the Invention

It the following, the present invention will be described in detail in conjunction with the embodiments:

Embodiment 1

One weight part of the raw material, containing 10 wt % of alcohol and 90 wt % of water, was supplied to the portion at 3 m from the top of the countercurrent flow extractor of packed column type of 50 mm in inner diameter and 10 m in length. Propane solvent of $2 \sim 10$ weight parts was supplied from the bottom of said extractor, and the temperature at the recovery stage was changed to various values for the tests. Alcohol concentrations at the top and bottom of said extractor were analyzed. The results are shown in Table 1. The temperature at the concentration stage was maintained at 40° C. Alcohol concentration at the top of extractor was within 95~97 wt % (free from propane) in all cases.

Alcohol recovery ratio was determined with the value of 99 wt % according to the conventional distillation method as standard. The recovery ratio higher than 99 wt % was regarded as acceptable (○), the value less than 95 wt % was rejected (×), and the value higher than 96 wt % but lower than 99 wt % was regarded as conditionally acceptable (Δ).

These results lead to the following findings:

The quantity of propane solvent could be extensively reduced by maintaining the temperature on the recovery stage at 90°~170° C., and most desirably at 100°~130° C. (3 weight parts of propane solvent was found enough to 1 weight part of 10% aqueous solution of alcohol.)

The pressure at 50-300 atm. brought the satisfactory results.

TABLE 1

Results of the Embodiment 1

| Weight ratio of propane solvent to raw material (—) | Temperature at recovery stage (°C.) | Pressure at recovery (atm) | Alcohol recovery ratio (wt %) | Evaluation |
|---|---|---|---|---|
| 2 | 40 | 100 | 70 | x |
| 2 | 100 | 100 | 90 | x |
| 3 | 40 | 100 | 80 | x |
| 3 | 60 | 100 | 90 | x |
| 3 | 90 | 100 | 99.0 | ○ |
| 3 | 100 | 100 | 99.1 | ○ |
| 3 | 110 | 50 | 99.0 | ○ |
| 3 | 110 | 100 | 99.1 | ○ |
| 3 | 110 | 200 | 99.3 | ○ |
| 3 | 110 | 250 | 99.6 | ○ |
| 3 | 110 | 300 | 99.8 | ○ |
| 3 | 120 | 100 | 99.2 | ○ |
| 3 | 130 | 100 | 99.1 | ○ |
| 3 | 150 | 100 | 98.9 | Δ |
| 3 | 170 | 100 | 98.6 | Δ |
| 3 | 200 | 100 | 93 | x |
| 4 | 120 | 100 | 99.4 | ○ |
| 6 | 120 | 100 | 99.6 | ○ |
| 10 | 120 | 100 | 99.9 | ○ |

Embodiment 2

The countercurrent flow extractor as described in Embodiment 1 was used. 3 weight parts of propane was supplied to 1 weight part of alcohol solution. The pressure at the recovery stage was maintained at the same level as that of the concentration stage, and the temperature at the recovery stage was kept at 110° C. The temperature at the concentration stage was changed to various values, and the tests were performed. The results are shown in Table 2.

When alcohol concentration in the solvent phase at the top of the tower was 95 wt % or more, which is the standard value for hydrate alcohol product, it was judged as acceptable (○).

As the result, it was found that the hydrate alcohol could have been condensed to 95 wt % or higher when the temperature at the condensation unit was kept to 10°~70° C., more desirably to 10°~50° C.

TABLE 2

Results of Embodiment 2

| Temperature at concentration stage (°C.) | Pressure at concentration stage (atm) | Alcohol concentration at the top of the tower (wt %; free from solvent) | Evaluation |
|---|---|---|---|
| 10 | 100 | 98 | ○ |
| 20 | 100 | 98 | ○ |
| 30 | 100 | 97 | ○ |
| 40 | 50 | 96 | ○ |
| 40 | 100 | 96 | ○ |
| 40 | 200 | 97 | ○ |
| 40 | 300 | 97 | ○ |
| 50 | 100 | 96 | ○ |
| 60 | 100 | 95 | ○ |
| 70 | 100 | 95 | ○ |
| 80 | 100 | 92 | x |
| 90 | 100 | 91 | x |
| 100 | 100 | 90 | x |

Embodiment 3

Next, an embodiment according to the flow in FIG. 2 is explained.

One weight part of raw material, containing 10 wt % of alcohol and 90 wt % of water was supplied from the line (2) to the portion at 3 m from the top of the countercurrent flow extractor (1) of packed column type, packed with 3 mm dixon packing of 50 mm in inner diameter and 10 m in length. Propane solvent of 2~10 weight parts was sent from the line (3) above said extractor (1) through spiral pipe (8) and is supplied from the distributor (9) at the bottom of said extractor (1). The pressure is adjusted to 100 kg/cm$^2$G by pressure control valve (10) from the top of said extractor (1), and propane solvent phase was sent to the propane solvent distillation tower (11).

The propane solvent distillation tower (11) is packed with 3 mm dixon packing of 100 mm in inner diameter and 5 m in length. The propane solvent phase from the top of said countercurrent flow extractor was introduced at the position 2 m from the bottom. Distillation was performed under the pressure of 26 atm. with temperature on the tower top at 65° C. and on the tower bottom at 70° C. The propane gas withdrawn from the tower top through the line (12) was compressed to 105 kg/cm$^2$G by the booster pump (14), and a part of it was sent to the bottom of the propane solvent distillation tower (11) through the line (22), and the remainder was sent to the line (18) through bypass line (16), and a part of it was returned to the propane solvent distillation tower (11) at the return ratio of 0.3. The other was circulated and supplied from the line (3) to said countercurrent flow extractor (1), and the operation was continued until it was turned to steady state.

Table 3 shows the alcohol recovery ratio and alcohol concentration when the temperature of raw material and propane solvent was changed to various values.

TABLE 3

| | | | | | Results of Embodiment 3 | | | | |
|---|---|---|---|---|---|---|---|---|---|
| Weight ratio of propane to raw material | Temperature of raw material (Line 2) (°C.) | Temperature of solvent (Line 3) (°C.) | Pressure at countercurrent flow extractor (atm) | Alcohol recovery ratio at countercurrent flow extractor (wt %) | Alcohol concentration at tower top of countercurrent flow extractor (Line 5) (wt %; free from propane) | Alcohol concentration at tower bottom of distillation tower (11) (Line 13) (wt %; free from propane) | Average temperature at recovery stage (7) of countercurrent flow extractor (1) (°C.) | Average temperature at concentration stage (6) of counter-current flow extractor (1) (°C.) | Evaluation |
| 2 | 120 | 40 | 100 | 99.0 | 95.7 | 98.9 | 117 | 65 | x |
| 3 | 120 | 40 | 100 | 98.9 | 95.7 | 99.0 | 108 | 60 | o |
| 4 | 120 | 40 | 100 | 99.9 | 96.0 | 99.3 | 103 | 55 | o |
| 8 | 120 | 40 | 100 | 99.8 | 95.9 | 99.2 | 95 | 47 | o |
| 10 | 120 | 40 | 100 | 99.9 | 96.3 | 99.8 | 90 | 45 | o |
| 4 | 120 | 10 | 100 | 99.9 | 97.0 | 99.9 | 91 | 37 | o |
| 4 | 120 | 70 | 100 | 99.7 | 95.0 | 98.9 | 110 | 75 | o |

COMPARATIVE EXAMPLE 1

The same countercurrent flow extractor and the same aqueous solution of alcohol were used as in Embodiment 1. 3 weight parts of propane solvent were supplied. Temperature at the recovery stage and the concentration stage was kept at 40° C., and the pressure at 100 kg/cm²G.

In this case, alcohol concentration of 96 wt % was obtained from tower top, but alcohol was lost from tower bottom, and the alcohol recovery ratio was 71 wt %.

COMPARATIVE EXAMPLE 2

In the comparative example 1, the temperature at the recovery stage and at the condensation unit was controlled at 110° C. respectively. In this case, alcohol recovery ratio was 99.2 wt % and was regarded as acceptable, whereas alcohol concentration at the tower top was as low as 90 wt %.

COMPARATIVE EXAMPLE 3

The same countercurrent flow extractor and the same aqueous solution of alcohol as in Embodiment 1 were used. $CO_2$ was used instead of propane for the test, and the results shown in Table 4 were obtained.

In this case, the temperature at the concentration stage changed to 20°~100° C., and alcohol concentration at tower top was 91 wt % at maximum.

TABLE 4

| | Results of Comparative Example 3 | | | |
|---|---|---|---|---|
| Weight ratio of CO₂ solvent to raw material (—) | Temperature at recovery stage (°C.) | Pressure at recovery stage (atm) | Alcohol recovery ratio (wt %) | Evaluation |
| 2 | 40 | 100 | 50 | x |
| 3 | 40 | 100 | 60 | x |
| 3 | 100 | 100 | 62 | x |
| 4 | 100 | 100 | 63 | x |
| 6 | 100 | 100 | 65 | x |
| 10 | 100 | 100 | 70 | x |
| 15 | 100 | 100 | 74 | x |
| 20 | 100 | 100 | 80 | x |
| 20 | 40 | 100 | 88 | x |

Effects of the Invention

As already described in detail, the present invention proposes, in the process of concentration and recovery of alcohol from aqueous solution of alcohol by the use of propane solvent, to use the propane in supercritical or pseudocritical conditions, to extract and recover alcohol of 99 wt % or higher by small quantity of propane, and further to concentrate alcohol to the concentration of 95 wt % by increasing the selectivity of alcohol through cooling of propane in liquid state. The use of only small quantity of solvent makes it possible to design the equipment in compact form and to reduce energy consumption. Thus, the invention offers an economical and efficient method to obtain alcohol with the concentration of 95 wt % or higher.

We claim:

1. An apparatus for the concentration and purification of alcohol comprising:
    a countercurrent flow extractor having a top, a middle and a bottom, and including a distributor at said bottom and a propane solvent supply line at said top disposed within said extractor, wherein said propane solvent supply line is configured to function as a heat exchanger for sending propane solvent in one of a supercritical and pseudocritical condition from above to the distributor at said bottom,
    a feed line of aqueous solution of alcohol at said middle, a heavy liquid drawing line at said bottom and a light liquid drawing line at said top;
    a propane solvent distillation tower having a tower top and a tower bottom, said distillation tower connected with said light liquid drawing line and having a propane solvent drawing line at the tower top and a concentrated alcohol drawing line at the tower bottom; and
    a connecting line to connect said propane solvent drawing line with said propane solvent supply line of said countercurrent flow extractor through a booster pump and the tower bottom.
    said propane solvent supply line being configured in the form of a helical coil, wherein the number of windings per unit axial length of said coil above said alcohol feed line is greater than the number of windings per unit axial length of said coil below said alcohol feed line.

* * * * *